United States Patent
Ingenhoven et al.

(10) Patent No.: US 7,055,723 B2
(45) Date of Patent: Jun. 6, 2006

(54) DEVICE AND SYSTEM FOR DISPENSING OR ASPIRATING/DISPENSING LIQUID SAMPLES

(75) Inventors: Nikolaus Ingenhoven, Männedorf (CH); Agathe Hodac, Rapperswil (CH); Noa Schmid, Grabs (CH)

(73) Assignee: Tecan Trading AG, Männedorf (CH)

( * ) Notice: Subject to any disclaimer, the term of this patent is extended or adjusted under 35 U.S.C. 154(b) by 82 days.

(21) Appl. No.: 10/399,429

(22) PCT Filed: Oct. 29, 2001

(86) PCT No.: PCT/CH01/00639

§ 371 (c)(1),
(2), (4) Date: Aug. 20, 2003

(87) PCT Pub. No.: WO02/40165

PCT Pub. Date: May 23, 2002

(65) Prior Publication Data
US 2004/0020942 A1 Feb. 5, 2004

(30) Foreign Application Priority Data
Nov. 17, 2000 (CH) .................... 2252/00
Nov. 29, 2000 (CH) .................... 2314/00
Dec. 12, 2000 (CH) .................... 2413/00

(51) Int. Cl.
*B67D 3/00* (2006.01)
(52) U.S. Cl. .................... 222/504; 222/135
(58) Field of Classification Search ............. 222/504, 222/135, 420, 422, 63, 61, 559, 386.5, 386, 222/401, 385, 383.2; 251/129.17, 129.06; 422/100
See application file for complete search history.

(56) References Cited

U.S. PATENT DOCUMENTS

| | | | | |
|---|---|---|---|---|
| 3,329,964 A | * | 7/1967 | Mutschler et al. | 346/78 |
| 5,356,034 A | * | 10/1994 | Schlumberger | 222/61 |
| 5,405,050 A | * | 4/1995 | Walsh | 222/1 |
| 6,063,339 A | * | 5/2000 | Tisone et al. | 422/67 |
| 6,250,515 B1 | * | 6/2001 | Newbold et al. | 222/504 |
| 6,371,339 B1 | * | 4/2002 | White et al. | 222/413 |
| 6,467,700 B1 | * | 10/2002 | Vann et al. | 239/225.1 |
| 6,915,928 B1 | * | 7/2005 | Brooks | 222/504 |

FOREIGN PATENT DOCUMENTS

| | | | |
|---|---|---|---|
| EP | 1093856 A1 | * | 4/2001 |
| JP | 09327628 A | * | 12/1997 |
| WO | WO 00/01798 | * | 1/2000 |

* cited by examiner

*Primary Examiner*—Frederick C. Nicolas
(74) *Attorney, Agent, or Firm*—Notaro & Michalos, PC

(57) ABSTRACT

The invention relates to a device (1) for dispensing or aspirating/dispensing liquid samples, including a pump (2) and a micro-ejection device (3), the micro-ejection device (3) having a pulse generator (4) with a chamber (5). The pulse generator (4) is used to produce pressure waves in the liquid in order to cause the samples of a liquid to be dispensed. The micro-ejection device (3) also comprises an end piece (6) and a liquid line (7) which connects the pulse generator (4) to the end piece (6) the pulse generator comprises a micro-actuator (10) which is configured to function in the same direction as that in which the pressure wave leaves the chamber (5). The inventive devices are characterised in that the chamber (5), in the area of the end facing away from the end piece (6), or the corresponding connecting element (14) has a narrowed section (16) which restricts any expansion of the pressure waves in the direction of the pump (2). The invention also relates to systems with multiple devices of this type.

20 Claims, 2 Drawing Sheets

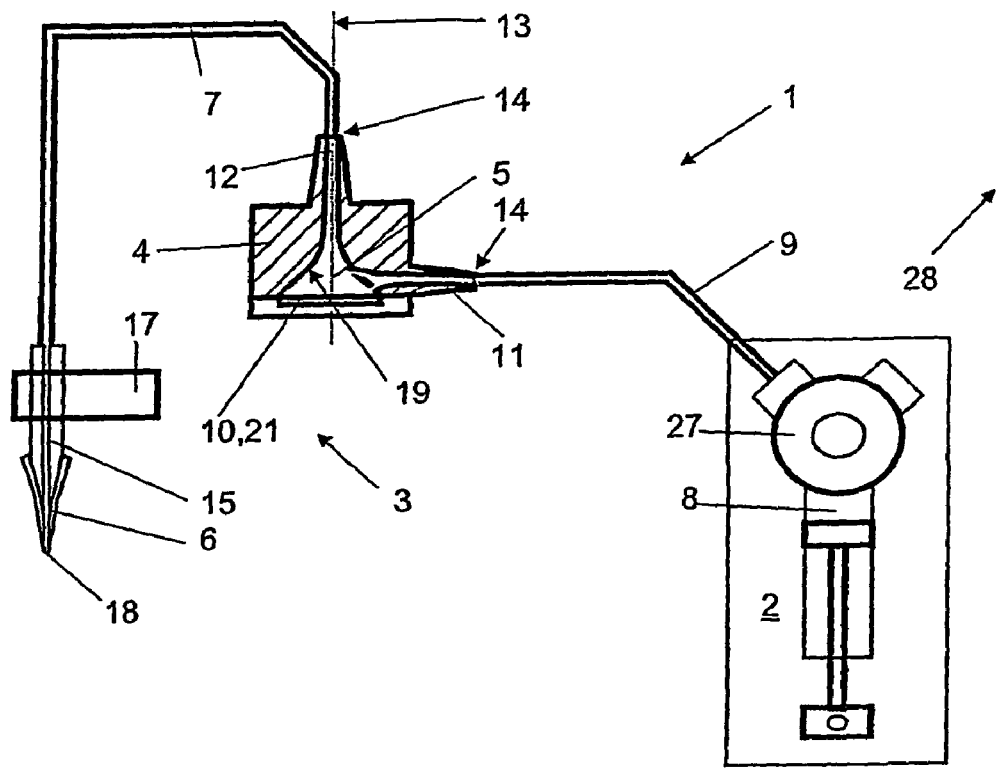
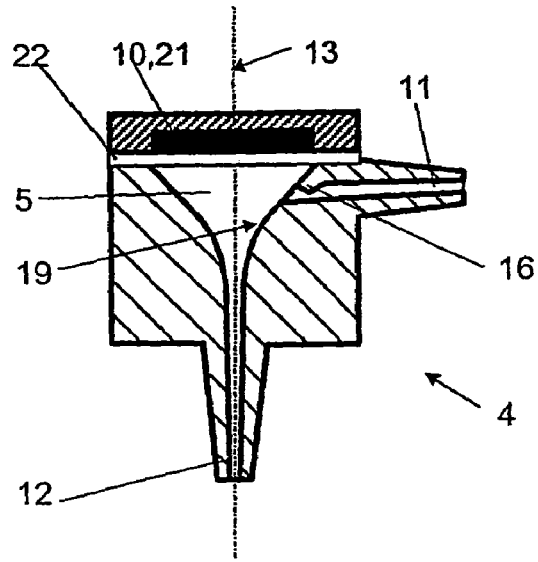
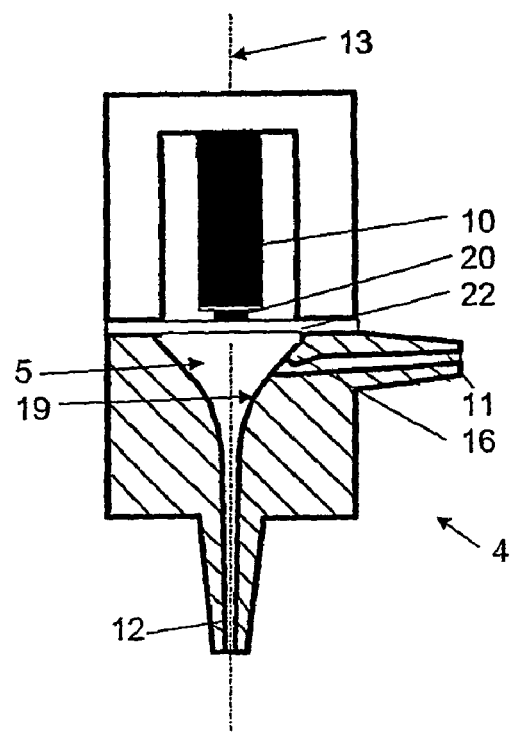

DEVICE AND SYSTEM FOR DISPENSING OR ASPIRATING/DISPENSING LIQUID SAMPLES

RELATED PATENT APPLICATIONS

This application claims priority of the Swiss patent application No. 2252/00 filed on Nov. 17, 2000, the Swiss patent application No. 2314/00 filed on Nov. 29, 2000, the Swiss patent application No. 2413/00 filed on Dec. 12, 2000, and the international application PCT/CH01/00639 filed on Oct. 29, 2001.

1. Field of the Invention

According to the preamble of the independent claim 1, the invention relates to a device for dispensing or aspirating/dispensing liquid samples, comprising a pump and a micro-ejection apparatus, with said micro-ejection apparatus having an impulse generator with a chamber and with said impulse generator being used to pressure waves in the liquid in order to cause the samples of a liquid to be dispensed, and with said micro-ejection apparatus further comprising an end piece and a liquid line which connects the impulse generator to the end piece and with the impulse generator comprising a micro-actuator which is configured to function in the same direction as that in which the pressure wave leaves the chamber. The invention further also relates to respective systems comprising such systems.

2. Prior Art

It is known that drops with a volume of more than 10 µl can be dispensed very easily from the air because drops will leave the tip of the pipette automatically when the pipette is handled correctly. The size of the drop is then determined by the physical properties of the sample liquid such as surface tension or viscosity. The size of the drop thus limits the resolution of the quantity of liquid to be dispensed.

The aspiration and dispensing, i.e. the pipetting, of liquid samples with a volume of less than 10 µl usually demands instruments and techniques which guarantee the dispensing of such small samples. The dispensing of a liquid with the tip of a pipette, i.e. with the end piece of an apparatus for dispensing or aspirating/dispensing liquid samples, can occur from the air ("from air") or by touching a surface. This surface can be the solid surface of a vessel ("on tip touch") to which the liquid sample is to be given. It can also be the surface of a liquid situated in this vessel ("on liquid surface"). A mixing process occurring subsequently to the dispensing is recommended especially in the case of very small sample volumes in the range of nanoliters or even picoliters, so that an even distribution of the sample volume within a diluent is ensured.

Disposable tips substantially reduce the likelihood of an undesirable transmission of sample particles (contamination). Known are simple disposable tips (so-called "air-displacement tips") whose geometry and material is optimized for the precise dispensing of very small volumes. The use of so-called "positive-displacement tips" which comprise a pump plunger on their inside is also known.

For the purpose of automating the pipetting process of volumes below 10 µl it is necessary to distinguish two processes from each other: The defined uptake (aspiration) and the subsequent delivery (dispensing) of liquid samples. Between such processes the tip of the pipette is usually moved by the experimenter or an automatic machine, so that the place of aspiration of a liquid sample differs from its dispensing point. For the precision of dispensing only the liquid system is relevant which consists of the pump (diluter), liquid line and end piece (tip of pipette). Among the many possible pumps for high-precision aspiration and dispensing of liquids, commercially obtainable devices with the names "CAVRO XL 3000 Modular Digital Pump" or "CAVRO XP 3000 plus Modular Digital Pump" have proven their worth. They are supplied by Cavro Scientific Instruments Inc., Sunnyvale, Calif., USA. Such pumps comprise a cylinder with a plunger which is movable therein and a stepper motor for driving the plunger. The stepper motor operates with a voltage of 24 V and is triggered by an external computer or microprocessor. Further details are shown in the operating manual "Operators Manual P/N 724043C" of Cavro Scientific Instruments Inc.

An apparatus of this kind and a respective method are known from U.S. Pat. No. 5,763,278. It concerns automatic pipetting of small volumes, with the apparatus comprising a pipetting needle, a diluter with a liquid output with a syringe and a valve. The syringe comprises a plunger and a plunger drive. A tubing connects the needle and the liquid output of the diluter, with the diluter and the tubing containing a substantially incompressible liquid. An impulse generator is arranged in the apparatus and connected with the incompressible liquid in the tubing, so that mechanical impulses with a force of at least 0.01 Ns can be emitted directly into the liquid of the tubing. Such an impulse is used to drive the liquid from the needle. The drop size is defined by a purposeful advance of the diluter plunger and the drop is ejected from the needle with an impulse. As a result of the definition of the volume with the diluter, the size of the drop and its reproducibility depends on the resolution of the diluter and is limited by the same.

OBJECTS AND SUMMARY OF THE INVENTION

It is the object of the present invention to provide a device for dispensing or aspirating/dispensing liquid samples up to the picoliter range in which the dispensed drop size and its reproducibility does not depend on the resolution of the diluter.

This object is achieved by the features of the independent claim 1. Additional features arise from the dependent claims.

This invention relates to a device (1) for dispensing or aspirating/dispensing liquid samples, comprising a pump (2) and a micro-ejection apparatus (3), with said micro-ejection apparatus (3) having an impulse generator (4) with a chamber (5). Said impulse generator (4) being used to produce pressure waves in the liquid in order to cause the samples of a liquid to be dispensed. The micro-ejection apparatus (3) further comprises an end piece (6) and a tubing (7) for the liquid which connects the impulse generator (4) to the end piece (6). The impulse generator comprising a micro-actuator (10) which is configured to function in the same direction as that in which the pressure wave leaves the chamber (5). The inventive devices are characterized in that the device (1), in the area of the end of the chamber (5) averted from the end piece (6), comprises a narrowed section (16) which is open during the production of the pressure waves and which restricts any propagation of the pressure waves in the direction towards the pump (2).

BRIEF DESCRIPTION OF THE DRAWINGS

The present invention will now be explained in more detail by reference to schematic drawings which illustrate preferable embodiments and shall not limit the scope of the present invention, wherein:

FIG. 1 shows diagrammatic view of a device for dispensing or aspirating/dispensing liquid samples;

FIG. 2 shows a sectional view through an impulse generator according to a first embodiment;

FIG. 3 shows a sectional view through an impulse generator according to a second embodiment;

DESCRIPTION OF THE INVENTION

Figure 4:
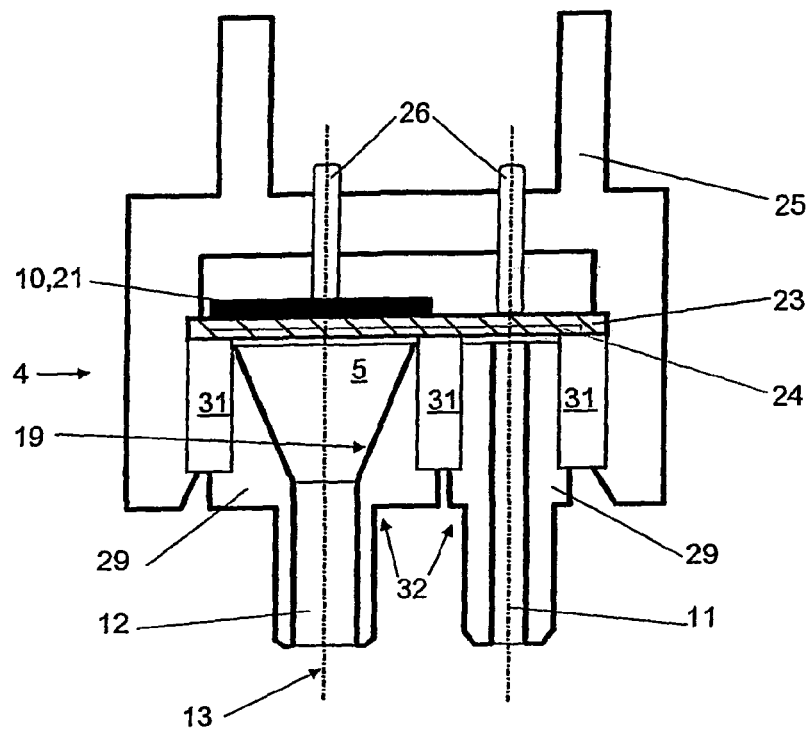
FIG. 4 shows a sectional view through an impulse generator according to a third embodiment.

FIG. 1 shows a diagrammatic view of a device for dispensing or aspirating/dispensing liquid samples according to a first embodiment. Said device 1 comprises a pump 2 and a micro-ejection apparatus 3. The micro-ejection apparatus comprises an impulse generator 4 with a chamber 5 and is filled completely with a liquid which thus forms a continuous liquid column. The impulse generator 4 is arranged in such a way that, for the purpose of producing the dispensing of liquid samples, pressure waves can be produced in the liquid. The micro-ejection apparatus 3 further comprises an end piece 6 and a liquid tubing 7. The liquid tubing 7 has a length of approx. 1 m in an embodiment and connects the impulse generator 4 with the end piece 6. The inside diameter of said tubing 7 is 0.8 mm in this embodiment and the wall thickness measures 0.6 mm.

Preferably, the pump 2 is a reciprocating pump or a diluter of type "CAVRO XP 3000 plus Modular Digital Pump". The cylinder 8 of the diluter has a volume in the range of 50 to 500 µl and the resolution of the diluter lies in the region of 3,000 steps or 6,000, 12,000 or 24,000 partial steps per entire stroke. The diluter is used in order to fill the tip of the pipette or the end piece 6. This comprises both the aspiration of a sample volume as well as the compensation of a dispensed volume during dispensing. The diluter or the pump 2 and the impulse generator 4 are mutually connected by way of a liquid tubing 9. The inside diameter of the tubings 7, 9 which are preferably made of tetrafluoroethylene-hexafluoropropylene-copolymer (FEP) is preferably 0.1 to 4 mm, with a diameter of 0.1 to 1 mm being especially preferable. For all tubings 7, 9 ("tubing") a wall thickness of 0.3 to 1.2 mm is preferable.

The impulse generator 4 comprises a chamber 5 and a micro-actuator 10 and is arranged in the device 1 for dispensing or aspiring/dispensing liquid samples between diluter or pump 2 and disposable tip or end piece 6. The micro-actuator 10 can comprise a piezo-element (e.g. as a stacked actuator or as a bimorph element), a magnetic element or a thermal actuating system. The common aspect of all these micro-actuators is that they produce a pressure wave in the liquid, such that a mechanical impulse is transmitted onto said liquid. Whereas piezo-actuators act through a sudden expansion and magnetic actuators accelerate a solenoid, thermal actuators suddenly heat a gas. Said gas is situated in a chamber enclosed with a membrane and suddenly expands when heated, so that the membrane moves and produces a pressure wave. The chamber 5 comprises an input channel 11 and an output channel 12. The micro-actuator 10 is preferably triggered by an electric square wave signal.

Every short pulse of this rectangular signal produces a sudden change in shape and/or position of the micro-actuator 10 which is transmitted as an impulse onto the liquid in chamber 5. Said impulse which is produced by the impulse generator 4 whose strength $\Delta p$ was calculated in an embodiment with 0.016 Ns initiates a pressure wave in the liquid which preferably spreads in the direction towards the output channel 12 of chamber 5 and leaves the chamber 5 there.

A chamber 5 which is preferably provided with rotationally symmetrical configuration and whose axis of symmetry 13 is arranged co-axially to the output channel 12 allows a substantially even propagation of said pressure wave in the chamber 5. Preferably, the micro-actuator 10 is arranged in the chamber in such a way that it acts in the same direction in which the pressure wave leaves the chamber 5. Since the entire micro-ejection apparatus 3 is always completely filled with a continuous liquid column, the volume of a dispensed liquid sample is defined alone by the parameters of a single impulse produced by the impulse generator 4.

In order to enable a substantially continuous propagation of the pressure wave through tubing 7 to the end piece 6, the chamber 5, the liquid tubing 7, the end piece 6 and all other connection elements 14 which may also be additionally provided comprise substantially continuous transitions and a similarly constant inside diameter. Said inside diameter is preferably always larger than the opening diameter 18 of the end piece 6. Under these preconditions the preferred wall thickness at the end of tip adapter 15 which carries the end piece 6 is less than 0.5 mm in the region of the transition to the tubing 7 and to the end piece 6. Preferably, all other transitions between impulse generator 4 and end piece 6 are adjusted accordingly.

In order to obstruct the propagation of the wave in the direction towards the pump 2, the chamber 5 is preferably provided in the region of its end averted from the end piece 6, i.e. in the zone of input channel 11, with a narrowed section 16. If the chamber 5 and the tubing 9 are connected to an additional connection element 14, said connection element 14 can also be provided with such a narrowed section 16.

The end piece 6 is arranged as a disposable tip of type "air-displacement tip", consists of a polymer material which is injection-molded for example and can be replaced after use as required. The end piece 6 preferable sits on a tip adapter 15 which forms a piece of the tubing 7 and is held and guided by an experimenter or a robot arm 17. The opening diameter 18 of the end piece 6 or the disposable tip is preferably 20 to 150 µm for the dispensing of samples in the nanoliter range. A diameter of less than 50 µm is especially preferable for dispensing samples in the picoliter range. Said opening diameter 18, as also the other geometry of the end piece 6, can be adjusted as needed to the properties of the liquid to be pipetted or the intended volume of the samples to be separated. In an embodiment the opening diameter 18 is approx. 50 µm.

FIG. 2 shows a sectional view through an impulse generator 4, according to FIG. 1 and according to a first embodiment. The axis of symmetry 13 lies co-axially to the output channel 12. At a right angle to the axis of symmetry 13 there is a micro-actuator with a bimorphous piezo-element 21 which closes off the chamber 5 on the rear side. The input channel 11 is provided on its transition to the inner wall 19 of chamber 5 with a narrowed section 16.

FIG. 3 shows a sectional view through an impulse generator 4 according to a second embodiment. The axis of symmetry 13 lies co-axially to the output channel 12. A micro-actuator 10 which operates on a magnetic basis is arranged at a right angle to the axis of symmetry 13. A membrane 22 for transmitting impulses onto the liquid in the chamber 5 is arranged between the actuator arranged as a solenoid 20 and the chamber 5. Said membrane 22 closes off the chamber 5 at the rear side. Instead of a solenoid working on a magnetic basis it would also be possible to use a stack of piezo-elements (not shown). The input channel 11 is provided at its transition point to the inner wall 19 of chamber 5 with a narrowed section 16.

FIG. 4 shows a sectional view through an impulse generator 4 according to a third embodiment. The axis of symmetry 13 lies co-axially to the output channel 12. A piezo-element 21 is arranged as a micro-actuator 10 at a right angle to the axis of symmetry 13 and is glued onto a silicon plate 23. The chamber 5 is thus closed off on the rear side with the silicon plate 23. The silicon plate 23, which is arranged between the micro-actuator 10 and the chamber 5, transmits the impulses onto the liquid in chamber 5. In contrast to the previously explained examples, the input channel 11 is arranged parallel to the output channel 12. The input channel 11 is connected with the chamber 5 via a connection channel 24 which is etched into the silicon plate 23. Said connection channel 24 has a very small cross section, so that in addition to the function of guiding the liquid it also fulfils the function of a constriction 16. Moreover, the inner diameter of the input channel 11 is far smaller than that of the output channel 12. The entire arrangement according to said third embodiment is held by an adapter 25. Said adapter 25 also comprises the electric contacts 26 for the piezo-element 21 of the micro-actuator 10. Preferably, a compartmenting structure 31 which reaches up to the upper side of the components 29 forming the chamber 5 is connected in a sealing fashion with the components 29. Said compartmenting structure 31 preferably is a glass plate with compartments 32 incorporated therein for receiving the components 29. The use of a glass plate comes with the advantage that a plane surface 33 is created for receiving the silicon plate 23. The silicon plate 23 and the glass plate can thus advantageously be mutually connected in an anodic fashion without any use of adhesives.

A system for dispensing or aspirating/dispensing liquid samples such as an automatic pipetting machine can comprise one (see FIG. 1) or several devices 1 (not shown). Automatic pipetting machines with eight channels are preferred, i.e. with eight end pieces 6, with which standard microtiter plates™ (trademark of Beckman Coulter, Inc., 4300 N. Harbour Blvd., P.O. Box 3100 Fullerton, Calif., USA 92834) or microplates with 96 wells with liquid samples can be charged.

Such systems can comprise the combination of 1 to n pumps 2 and 1 to n impulse generators 4 with the same number each. Similar systems can comprise the combination of a single pump 2 with several impulse generators 2. Preferred are automatic pipetting machines with eight channels, i.e. with eight impulse generators 4 and eight end pieces 6. The end pieces 6 are preferably arranged in a one-dimensional array in the form of a row, so that it is possible to work with 8, 32, 72 or 128 channels simultaneously and parallel. Similar systems can comprise a two-dimensional array of end pieces 6 in the form of a grid, so that microplates with 384, 864, 1536 or even more flat-bottom blocks can be charged simultaneously. Combinations of the aforementioned systems are also possible, so that a system will simultaneously comprise end pieces 6 which are arranged and/or movable in a linear or planar array. If a system comprises several impulse generators 4, they can be arranged on a single component, e.g. in the form of an array of units. In a further preferred embodiment of a system in accordance with the invention for dispensing or aspirating/dispensing liquid samples, the end pieces 6 are attached directly to the impulse generators 4 which are arranged on a two-dimensional array and on a common component (see FIG. 5).

Preferably, the individual impulse generators 4 and pumps 2 are each addressable and controllable in such systems via a control unit, e.g. via a personal computer which is equipped with the respective hardware and software.

A three-way valve 27 and at least one storage reservoir 28 which is connected to the same is preferable especially for multi-channel systems with a large liquid throughput. System liquid or even a liquid to be dispensed can be situated in the storage reservoir. Several storage reservoirs are preferably used in systems with several pumps.

Figure 5:
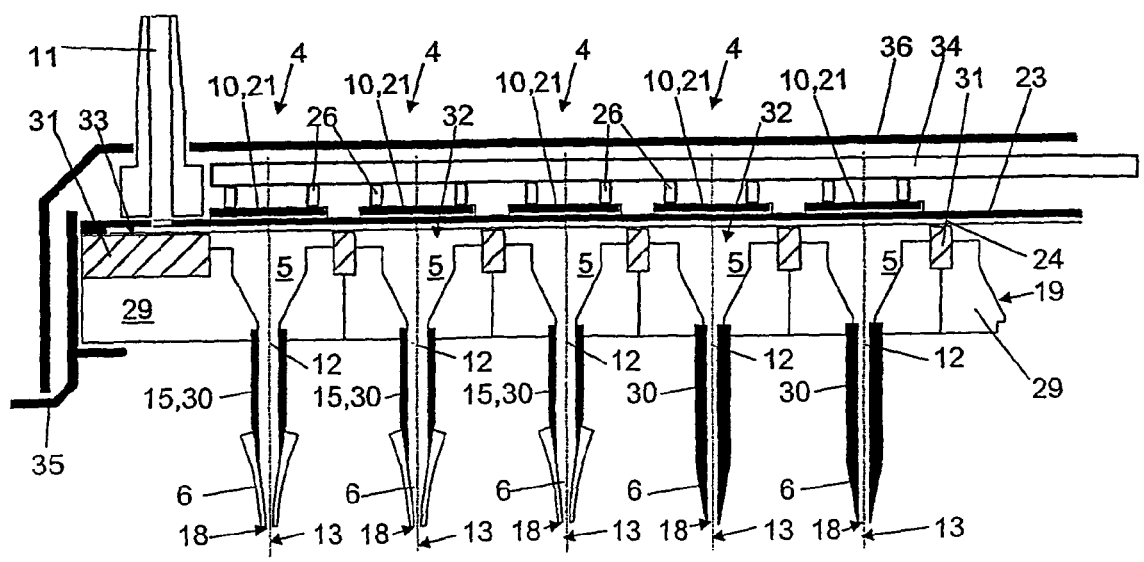
FIG. 5 shows a sectional view through an array of impulse generators according to a fourth embodiment.

FIG. 5 shows a sectional view through an array of impulse generators according to a fourth embodiment. The individual chambers 5 of the adjacently arranged impulse generators 4 are arranged in a component 29 which consists of a polymer material which is integrally injection-molded or turned individually from solid material for example. Needles 30 are arranged co-axially with the axis of symmetry 13 of chambers 5 and form the output channel 12 of the same. Preferably, said needles 30 consist of stainless steel and taper to a point at their free end in such a way that they can either be used directly as end pieces 6 (i.e. as pipette tips) or they each can receive a disposable tip.

In a partial or even close contact with said component 29, a compartmenting structure 31 is sealingly connected with the component 29 on its upper side. Said compartmenting structure 31 preferably consists of a glass plate from which compartments 32 are arranged in such a way that they correspond in the register with the chambers 5. The use of a glass plate leads to the advantage that a plane surface 33 is created. Advantageously the silicon plate 23 and the glass plate can be connected with each other in an anodic fashion without using any adhesives.

To said surface 33 a thin silicon plate 23 is applied into which connecting channels 24 are etched. Micro-actuators 10 in the form of piezo-elements 21 are arranged on the side of the silicon plate 23 which is averted from the chamber, which piezo-elements correspond with respect to their distribution to the pattern of the underlying chamber arrangement. The impulses required for ejecting a sample are thus produced by the piezo-elements 21 and transmitted onto the liquid via the silicon plate 23. All chambers 5 are connected with each other and with the input channel 11 leading to the diluter or pump 2 by way of the connecting channels 24 which have a cross section which is small in relationship to the output channels 12, so that all said hollow chambers as well as the needles 30 (and if disposable tips are used they too) are always filled completely with a liquid column. This ensures on the one hand that the connecting channels representative of a constriction obstruct a propagation of the pressure waves in the direction towards pump 2 and that the volume of the liquid samples issued from the end pieces 6 is defined solely by the parameters of the impulses generated by the impulse generators 4.

The electronic system required for triggering the individual piezo-elements 21 as well as the respective electrical feed lines can be arranged on a common component 34 also in a manner corresponding to the distribution of the chambers 5 and the micro-actuators 10. A housing (not shown) which preferably consists of a bottom shell 35 and an upper'shell 36 preferably comprises the entire array with the impulse generators 4 and the associated electronic system on the component 34. Such an array may comprise a number of eight impulse generators for example or even a surface area of 96 or 384 impulse generators for example.

A system for dispensing or aspirating/dispensing liquid samples works as follows for example:
1. The robotic arm 17 takes up a disposable tip from a storage location, with the conical, mutually adjusted shape of tip adapter 15 and disposable tip guaranteeing a favorable fit and sealing.
2. The disposable tip is filled completely with a system liquid (e.g. with distilled or de-ionized water) by means of the diluter or by means of pump 2.
3. The robotic arm 17 moves to a receptacle in which the liquid to be pipetted is located and is lowered there until the end piece 6 or the pipette tip touches the liquid surface. A defined volume of the liquid is received by the end piece 6 (aspiration) with the pump 2.
4. The robotic arm 17 moves to a predetermined delivery point where the impulse generator 4 emits a precisely defined, short impulse. This initiates a pressure wave in the liquid which propagates in the chamber 5 of the impulse generator 4 in the direction towards the output channel 12, through the tubing 7 and finally through the end piece 6. The end piece 6 forms the narrowest point on the entire route which the pressure wave needs to cover so that the same is subjected to an acceleration in the end piece 6. Once the speed of the pressure wave is so high that it overcomes the surface tension forces of the liquid, sample volumes of a specific and defined magnitude are ejected. The pipette diameter, i.e. the opening diameter 18 of the end piece 6, has an influence that cannot be neglected on the resulting sample volume or drop size which lies in the range of 0.01 to 10 nl. The dispensed total volume is obtained from the volume of a single separated sample (drop) and the number of the impulses emitted by the impulse generator (dispensing).
5. During the dispensing, the piston of the pump 2 follows up, so that substantially the dispensed volume of liquid is compensated.
6. After dispensing a predetermined quantity of sample liquid, the robotic arm 17 moves the end piece 6 over a waste collection point where the disposable tip is ejected. A new tip is then picked up.

The respective parts were provided with the same reference numerals in all figures.

What is claimed is:

1. A device for dispensing or aspirating/dispensing liquid samples, comprising a pump and a micro-ejection apparatus, with said micro-ejection apparatus having an impulse generator with a chamber and with said impulse generator being used to produce pressure waves in the liquid in order to cause the samples of a liquid to be dispensed, and with said micro-ejection apparatus further comprising an end piece and a tubing for the liquid which connects the impulse generator to the end piece and with the impulse generator comprising a micro-actuator which is configured to function in the same direction as that in which the pressure wave leaves the chamber,
wherein the device, in the area of the end of the chamber averted from the end piece, comprises a narrowed section which is open during the production of the pressure waves and which restricts any propagation of the pressure waves in the direction towards the pump.

2. The device of claim 1, wherein a corresponding connecting element comprises the narrowed section.

3. The device of claim 1, wherein the entire micro-ejection apparatus is filled completely with a continuous liquid column and that the volume of a dispensed liquid sample is defined alone by the parameters of a single pulse produced by the impulse generator.

4. The device of claim 1, with the chamber of the impulse generator comprising at least one inner wall and/or one connecting element with which the chamber is connected to the tubing for the liquid,
wherein the chamber, end piece, tubing and/or connecting elements, for the purpose of enabling a continuous propagation of the pressure waves through the tubing, form substantially continuous transition points up to the end piece and also a substantially constant inside diameter, with said inside diameter being larger than the opening diameter of the end piece.

5. The device of claim 1, wherein the tubings have an inside diameter of 0.1 to 4 mm, especially 0.1 to 1 mm, and a wall thickness of 0.3 to 1.2 mm.

6. The device of claim 1, wherein the end piece is arranged as a pipette tip which is disposable and can be replaced after each use.

7. The device of claim 1, wherein the end piece has an opening diameter of 20 to 150 µm for dispensing sample volumes in the nanoliter range.

8. The device of claim 1, wherein the end piece has an opening diameter of less than 50 µm for dispensing sample volumes in the picoliter range.

9. The device of claim 1, wherein during the dispensing of liquid samples from the end piece the pump is provided with a configuration that allows it to be triggered for replenishing liquid.

10. The device of claim 1, wherein the pump is provided with a configuration that allows it to be triggered for the aspiration of liquid.

11. The device of claim 1, wherein the impulse generator comprises a membrane actuated by at least one of a group comprising a bimorph piezo-element, a piezo stack, a solenoid and a thermal actuator.

12. The device of claim 1, wherein the pump is a piston pump which comprises a cylinder, a piston and a drive.

13. A system with a device according to claim 1, the system comprising a plurality of end pieces and associated tubings and impulse generators.

14. The system of claim 13, which comprises several pumps (2).

15. The system of claim 13, which comprises a three-way valve connected upstream of the pump or the pumps and at least one storage reservoir connected to the same.

16. The system of claim 13, which is arranged to receive sample volumes of at least 1 nl.

17. The system of claim 13, which is configured to dispense sample volumes of at least 0.01 nl.

18. The system of claim 13, wherein the individual impulse generators and pumps can be addressed individually via a control unit.

19. The system of claim 13, which comprises a one-dimensional or two-dimensional array of end pieces.

20. The system of claim 13, wherein the plurality of impulse generators are arranged on a single component.

* * * * *